(12) United States Patent
Kitamura

(10) Patent No.: US 8,829,228 B2
(45) Date of Patent: Sep. 9, 2014

(54) CARBOXYLATE COMPOUND AND METHOD OF PRODUCING THE SAME AND PERFUME COMPOSITION THEREOF

(75) Inventor: Mitsuharu Kitamura, Kurashiki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 13/822,460

(22) PCT Filed: Nov. 1, 2011

(86) PCT No.: PCT/JP2011/006125
§ 371 (c)(1),
(2), (4) Date: Mar. 12, 2013

(87) PCT Pub. No.: WO2012/063433
PCT Pub. Date: May 18, 2012

(65) Prior Publication Data
US 2013/0184486 A1  Jul. 18, 2013

(30) Foreign Application Priority Data
Nov. 12, 2010  (JP) .................................. 2010-254188

(51) Int. Cl.
*C07C 67/38* (2006.01)
*C07C 69/753* (2006.01)
*C11B 9/00* (2006.01)
*C07C 67/14* (2006.01)

(52) U.S. Cl.
CPC .............. *C07C 69/753* (2013.01); *C07C 67/38* (2013.01); *C11B 9/0046* (2013.01); *C07C 2102/42* (2013.01); *C07C 67/14* (2013.01)
USPC ...................................................... 560/114

(58) Field of Classification Search
None
See application file for complete search history.

(56) References Cited

U.S. PATENT DOCUMENTS

| | | | |
|---|---|---|---|
| 4,312,888 A | | 1/1982 | Klemarczyk et al. |
| 4,319,036 A | * | 3/1982 | Klemarczyk et al. ......... 560/120 |
| 4,350,823 A | | 9/1982 | Klemarczyk et al. |
| 4,442,025 A | | 4/1984 | Boelens et al. |

FOREIGN PATENT DOCUMENTS

| | | |
|---|---|---|
| CN | 1150807 A | 5/1997 |
| EP | 0 040 894 B1 | 1/1984 |
| GB | 000880788 A * | 10/1961 |
| JP | 57-008757 | 1/1982 |
| JP | 57-021350 | 2/1982 |

OTHER PUBLICATIONS

International Search Report issued Jan. 24, 2012 in PCT/JP2011/006125.
G. E. Gream, et al., "Synthesis of exo- and endo-2,3,3-Trimethylnorbornane-2-carboxylic Acid", Australian Journal of Chemistry, vol. 27, No. 3, Mar. 1974, pp. 543-565 (and cover page).
Mototaka Nakajima, "Basic Knowledge of Perfume and Flavor Blending", 1995, pp. 215, 235 and 244-246 (published by Sangyo-Tosho Co., Ltd).
Combined Office Action and Search Report issued Apr. 9, 2014 in Chinese Patent Application No. 201180054449.0 with English language translation and English Translation of Category of Cited Documents.
An Jing, et al., "Study on the Synthesis of Aliphatic Acid Ramification", Hebei Journal of Industrial Science & Technology, vol. 19, No. 5, (2002), pp. 24-28 (with English abstract).

* cited by examiner

*Primary Examiner* — Brandon Fetterolf
*Assistant Examiner* — Ana Z Muresan
(74) *Attorney, Agent, or Firm* — Oblon, Spivak, McClelland, Maier & Neustadt, L.L.P.

(57) ABSTRACT

There are provided a novel carboxylate compound useful as a blending perfume raw material and having a brisk pine-like odor and a method of producing the same and a perfume composition containing such a carboxylate compound.
The carboxylate compound of the invention is represented by a general formula (1):

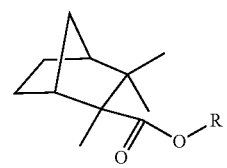

(1)

wherein R is an alkyl group having two to four carbon atoms.

10 Claims, No Drawings

CARBOXYLATE COMPOUND AND METHOD OF PRODUCING THE SAME AND PERFUME COMPOSITION THEREOF

TECHNICAL FIELD

This invention relates to a novel carboxylate compound and a method of producing the same and a perfume composition thereof, and more particularly to a novel carboxylate compound useful as a blending perfume raw material and a method of producing the same and a perfume composition containing the carboxylate compound.

BACKGROUND ART

It is known that compounds useful as a perfume are present among esters. For example, Non-patent Literature 1 discloses that geranyl acetate having a rose-like odor, methyl jasmonate having a jasmine-like sweet odor, FRUITATE having a fruity odor, methyl benzoate having a strong, dry fruity odor and so on are useful as a blending perfume material.

CITATION LIST

Non-Patent Literature

NPL 1: Mototaka Nakajima, "Basic Knowledge of Perfume and Flavor Blending" 1995, page 215, 235, 244~246, published by Sangyo-Tosho Co., Ltd.

SUMMARY OF INVENTION

Technical Problem

It is an object of the invention to provide a novel carboxylate compound useful as a blending perfume raw material and having a brisk pine-like odor and a method of producing the same and a perfume composition containing such a carboxylate compound.

Solution to Problem

The inventors have synthesized various compounds and made studies on their odors and found out that novel carboxylate compounds represented by the following general formula (1):

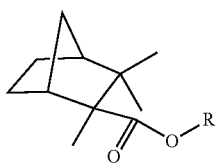

(wherein R is an alkyl group having two to four carbon atoms) have a brisk pine-like odor.

That is, the invention relates to a novel carboxylate compound and a method of producing such a carboxylate compound and a perfume composition containing such a carboxylate compound and is constituted as follows:

[1] A carboxylate compound represented by the following general formula (1):

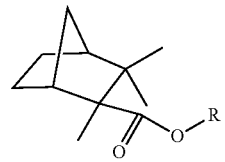

wherein R is an alkyl group having two to four carbon atoms.

[2] A perfume composition containing a carboxylate compound represented by the following general formula (1):

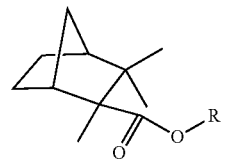

wherein R is an alkyl group having two to four carbon atoms.

[3] A method of producing a carboxylate compound represented by the following general formula (1):

wherein R is an alkyl group having two to four carbon atoms, which comprises reacting 2,2-dimethyl-3-methylene bicyclo[2,2,1]heptane represented by the following formula (2):

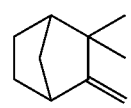

with carbon monoxide and subsequently with an alcohol having two to four carbon atoms in the presence of hydrogen fluoride.

Advantageous Effect of Invention

The carboxylate compounds according to the invention are novel in a point of having a brisk pine-like odor and have an excellent odor sustention, so that they are useful as a perfuming ingredient for a variety of products such as toiletry products, soaps, clothing detergents and the like. According to the production method of the carboxylate compound in the invention, it is possible to produce the carboxylate compounds by an industrially advantageous method.

DESCRIPTION OF EMBODIMENTS

<Novel Carboxylate Compound of General Formula (1)>

The novel carboxylate compounds according to the invention are represented by the general formula (1).

In the formula, R is an alkyl group having two to four carbon atoms. As the alkyl group having two to four carbon atoms, mention may be made of ethyl group, n-propyl group, iso-propyl group, n-butyl group, iso-butyl group and tert-butyl group. Among them, ethyl group and iso-propyl group are particularly preferable as R.

<Production Method of Novel Carboxylate Compound>

The carboxylate compounds represented by the general formula (1) according to the invention can be produced industrially advantageously by reacting a compound represented by the formula (2) with carbon monoxide in the presence of anhydrous hydrogen fluoride (which may be referred to as HF) to obtain an acid fluoride (formula (3)) and thereafter esterifying with an alcohol.

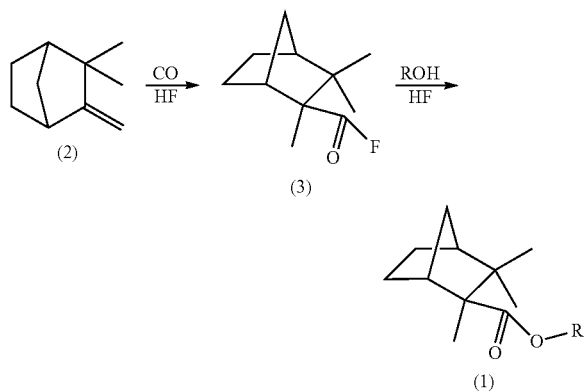

<Carbon Monoxide>

Carbon monoxide used in the carbonylation step may contain an inert gas such as nitrogen, methane or the like, but has a partial pressure of carbon monoxide of 0.5~5 MPa, preferably 1~3 MPa. When the partial pressure of carbon monoxide is not less than 0.5 MPa, the carbonylation reaction proceeds sufficiently, and an objective alicyclic carbonyl compound can be obtained in a high yield without combining with side reaction such as disproportionation, polymerization or the like. Also, the partial pressure of carbon monoxide is preferable to be not more than 5 MPa in view of equipment burden.

<Hydrogen Fluoride>

HF used in the carbonylation step is a solvent for the reaction, a catalyst and an auxiliary material, so that it is used at substantially an anhydrous state. The amount of HF used is 4~25 times, preferably 6~15 times per 1 mole of the compound of the formula (2) as a raw material. When the molar ratio of HF is 4 times or more, the carbonylation reaction proceeds efficiently and the side reaction such as disproportionation, polymerization or the like can be suppressed and an objective carbonyl compound can be obtained in a high yield. Also, HF is preferable to be used at a molar ratio of 25 times or less in view of raw material cost and productivity.

<Reaction Solvent>

In this reaction may be used a solvent well dissolving the raw materials and being inactive to HF. For example, a saturated hydrocarbon compound such as hexane, heptane, decane or the like can be used. The use of the solvent and the amount thereof are not particularly limited, and may be selected properly. The amount used to the compound of the formula (2) as a raw material is preferable to be 0.2~2.0 times by mass from a viewpoint that the polymerization reaction is suppressed to increase the yield and 0.5~1.0 times by mass in view of the productivity and energy efficiency.

<Reaction Conditions>

The type of the carbonylation reaction is not particularly limited, and may be any method of batch type, semi-continuous type, continuous type and the like.

The temperature of the carbonylation reaction is a range of −50° C.~30° C., preferably −30° C.~20° C. The reaction temperature is preferable to be not lower than −50° C. in view of the reaction rate. Also, when the reaction temperature exceeds 30° C., the amount of isomers produced is increased to not only lower the yield of an objective product but also deteriorate the purity of the product.

The reaction time is preferable to be 1~5 hours. When the reaction time is less than 1 hour, the reaction does not proceed sufficiently, while when it exceeds 5 hours, the apparatus becomes larger and the efficiency becomes poor.

The end point of the reaction is not particularly limited, but there is a time that absorption of carbon monoxide is stopped.

In the carbonylation reaction, an acid fluoride (formula (3)) is produced from HF and carbon monoxide.

The reaction solution of the resulting acid fluoride is purified by a usual method such as distillation or the like after the removal of excessive HF and may be used as a raw material in a subsequent esterification step. Commonly, there is adopted a method wherein the solution of the carbonylation reaction containing HF catalyst itself is reacted with an alcohol to produce a carboxylate compound.

The alcohol used in the invention is an alcohol having two to four carbon atoms.

The alcohol having two to four carbon atoms is not particularly limited, and may be properly selected depending upon the purposes. For example, mention may be made of ethanol, n-propanol, iso-propanol, n-butanol, iso-butanol, tert-butanol and so on.

Among them, ethanol, n-propanol, iso-propanol, n-butanol and iso-butanol are preferable.

The use amount of the alcohol having two to four carbon atoms is not particularly limited, and may be properly selected depending upon the purposes, but it is 0.5~2 times by mol, preferably 0.8~1.5 times by mol per the compound of the formula (2) as a raw material.

The esterification temperature is not lower than −20° C. but not higher than 20° C. from a viewpoint of improving the yield while suppressing side reaction. When it is lower than −20° C., the esterification rate is slow and the yield lowers. While when it exceeds 20° C., the decomposition of ester or dehydration reaction of the alcohol added is caused to increase a risk of by-producing water in the system.

The reaction time is preferable to be 0.5~3 hours. When the reaction time is shorter than 0.5 hour, the reaction does not proceed sufficiently, while when it exceeds 3 hours, the apparatus becomes large and the efficiency is poor. The end point of the reaction is not particularly limited, but there is a time that the rise of reaction heat is not observed.

The thus obtained esterified product is a solution of carboxylate/HF complex, which is decomposed into carboxylate and HF by heating and hence HF can be recovered and recycled by vaporization. The decomposition operation of this complex is necessary to be conducted as fast as possible for avoiding modification by heating, isomerization and the like of the product. In order to rapidly promote the heat decomposition of the complex, it is preferable to decompose the complex into HF under a reflux of an inert solvent (for example, a saturated aliphatic hydrocarbon such as heptane or the like, or an aromatic hydrocarbon such as benzene or the like). Also, when the reaction liquid is extracted into an ice water, it is separated into an oil phase and an aqueous phase by extracting from a bottom of an autoclave into an ice water, and thereafter the oil phase is washed with an aqueous solution of 2 mass % sodium hydroxide twice and with a distilled water twice and then dehydrated with anhydrous sodium sulfate. The thus obtained solution is further passed through an evaporator to remove low-boiling fractions and the like, and then subjected to rectification with a rectifier having a theoretical plate number of 20 to obtain a carboxylate compound as a product.

Preferably, the novel carboxylate compound represented by the general formula (1) can be included in a perfume composition according to the invention.

The carboxylate compound of the general formula (1) obtained according to the invention has a brisk pine-like odor and is excellent in the sustention, so that it can be used alone or in a combination with another ingredient as a perfuming ingredient for a variety of soap, shampoo, rinse, detergent, cosmetics, spray product, aromatic substance, perfumery, bath salts and so on. Also, it can be expected as a synthesis intermediate for use in foods, medicines, agrichemicals, liquid crystal and so on.

<Perfume Composition>

The perfume composition according to the invention is obtained by blending and compounding one or more of the novel carboxylate compounds of the general formula (1) into another perfume ingredient usually used or a blending perfume of a desired composition.

The amount to be compounded is varied depending upon the kind of the blending perfume, the type of the target odor, the strength of the odor and the like. However, the compound is preferably added to the blending perfume in an amount of 0.01~90 mass %, more preferably 0.1~50 mass %.

The other perfume ingredient capable of being used in a combination with the novel carboxylate compound according to the invention is not particularly limited and may be properly selected depending upon the purposes. For example, mention may be made of a surfactant such as polyoxyethylene laurylsulfate ether or the like; a solvent such as dipropylene glycol, diethyl phthalate, ethylene glycol, propylene glycol, methyl myristate, triethyl citrate or the like; hydrocarbons such as limonene, α-pinene, β-pinene, terpinene, cedrene, longifolene, valencene and the like; alcohols such as linalool, citronellol, geraniol, nerol, terpineol, dihydromyrcenol, ethyllinalool, farnesol, nerolidol, cis-3-hexenol, cedrol, menthol, borneol, β-phenylethyl alcohol, benzyl alcohol, phenyl hexanol, 2,2,6-trimethylcyclohexyl-3-hexanol, 1-(2-t-butyl-cyclohexyloxy)-2-butanol, 4-isopropylcyclohexane methanol, 4-methyl-2-(2-methylpropyl)tetrahydro-2H-pyrane-4-ol, 2-methyl-4-(2,2,3-trimethyl-3-cyclopentene-1-yl)-2-butene-1-ol, 2-ethyl-4-(2,2,3-trimethyl-3-cyclopentene-1-yl)-2-butene-1-ol, isocamphylcyclohexanol, 3,7-dimethyl-7-methoxyoctane-2-ol and the like; phenols such as eugenol, thymol, vanillin and the like; esters such as linalyl formate, citronellyl formate, geranyl formate, n-hexyl acetate, cis-3-hexenyl acetate, linalyl acetate, citronellyl acetate, geranyl acetate, nellyl acetate, terpinyl acetate, nopil acetate, bornyl acetate, isobronyl acetate, o-t-bytylcyclohexyl acetate, p-t-butylcyclohexyl acetate, tricyclodecenyl acetate, benzyl acetate, styralyl acetate, cinnamyl acetate, dimethylbenzylcarbinyl acetate, 3-pentyltetrahydropyrane-4-yl acetate, citronellyl propionate, tricycldecenyl propionate, allylcyclohexyl propionate, ethyl-2-cyclohexyl propionate, benzyl propionate, citronellyl butyrate, dimethylbenzylcarbinyl n-butyrate, tricyclodecenyl isobutyrate, methyl-2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyldihydro jasmonate, methyl-2,4-dihydroxy-3,6-dimethyl benzoate, ethylmethylphenyl glycidate, methyl anthranilate, FRUITATE and the like; aldehydes such as n-octanal, n-decanal, n-dodecanal, 2-methylundecanal, 10-undecenal, citronellal, citral, hydroxycitronellal, dimethyl tetrahydrobenzaldehyde, 4(3)-(4-hydroxy-4-methylpentyl)-3-cyclohexene-1-carboaldehyde, 2-cyclohexyl propanal, p-t-butyl-α-methylhydrocinnamic aldehyde, p-isopropyl-α-methylhydrocinnamic aldehyde, p-ethyl-α,α-dimethylhydrocinnamic aldehyde, α-amylcinnamic aldehyde, α-hexylcinnamic aldehyde, piperonal, α-methyl-3,4-methylenedioxyhydrocinnamic aldehyde and the like; ketones such as methylheptenone, 4-methylene-3,5,6,6-tetramethyl-2-heptanone, amylcyclopentanone, 3-methyl-2-(cis-2-pentene-1-yl)-2-cyclopentene-1-on, methylcyclopentenolone, roseketone, γ-methylionone, α-ionone, carbone, menthone, camphor, nootkatone, benzylacetone, anysilacetone, methyl-β-naphthylketone, 2,5-dimethyl-4-hydroxy-3(2H)-furanone, maltol, 7-acetyl-1,2,3,4,5,6,7,8-octahydro-1,1,6,7-tetramethyl naphthalene, muscone, civetone, cyclopentadecanone, cyclohexedecanone and the like; acetals and ketals such as acetoaldehyde ethylphenylpropyl acetal, citraldiethyl acetal, phenylacetoaldehyde glycerin acetal, ethylacetoacetate ethyleneglycol ketal and the like; ethers such as anetol, β-naphthylmethyl ether, β-naphthylethyl ether, limonene oxide, rose oxide, 1,8-cineol, racemic or photoactive dodecahydro-3a,6,6,9a-tetramethylnaphtho[2,1-b]furane and the like; nitriles such as citronerylnitrile and the like; lactones such as γ-nonalactone, γ-undecalactone, σ-decalactone, γ-jasmolactone, cumarin, cyclopentadecanolide, cyclohexadecanolide, ambretolide, ethylene brassylate, 11-oxahexadecanolide and the like; natural essential oils and natural extracts of orange, lemon, bergamot, mandarin, peppermint, spearmint, lavender, chamomile, rosemary, eucalyptus, sage, basil, rose, geranium, jasmine, ylang-ylang, anise, clove, ginger, nutmeg, cardamom, cedar, Japanese cypress, vetiver, patchouli, labdanum and the like. Moreover, these other perfume ingredients may be compounded alone or in a combination of two or more.

Since the carboxylate compound of the general formula (1) gives an excellent brisk pine-like odor, it can be used as a perfuming ingredient for a variety of products such as perfumery, health materials, sundry goods, foods, quasi drugs, medicines and so on.

The carboxylate compounds of the general formula (1) can be used as a perfuming ingredient for a flagrance product such as perfumed water, spray mist or the like; shampoo, rinse, hair tonic, hair cream, mousse, gel, pomade, spray and other cosmetics for hair; cosmetics for skin such as face lotion, serum, cream, milky lotion, facial mask, foundation, face powder, lip stick, various makeups and the like; dish detergent, laundry detergent, softener, disinfectant detergent, odor eliminating detergent, indoor aromatic substance, furniture cares, glass cleaner, furniture cleaner, floor cleaner, disinfectant, insecticide, bleaching agent and various other detergents for health; quasi drugs such as teeth paste, mouth wash, bath salts, adiaphoretic, perm liquid and the like; sundry goods such as toilet paper, tissue paper and the like; medicines; food and so on.

Also, the amount of the perfume composition according to the invention compounded into the product is not particularly limited, and may be properly selected depending upon the purposes. The amount of the carboxylate compound of the general formula (1) compounded to the product is preferably 0.001 mass %~50 mass %, more preferably 0.01 mass %~20 mass %.

EXAMPLES

The method of the invention will be further described in detail with reference to the following examples, but the invention is not limited to these examples.

<Gas Chromatography Analytical Conditions>

Gas chromatography is carried out by using GC-17A made by Shimadzu Corporation and HR-1 (0.32 mmφ×25 m×0.50 µm) made by ULBON as a capillary column. As a temperature rising condition, the temperature is raised from 100° C. to 300° C. at a rate of 5° C./min.

<GC-MS>

POLARIS Q of GC-MS spectrum device made by Thermo ELECTRON

<$^1$H-NMR Spectrum Analysis>

Device: EX-270 BRUKER AVANCE II 600 of $^1$H-NMR spectrum device made by JEOL Ltd.

Internal standard substance: tetramethylsilane (TMS)

<Yield, Isomer Ratio of Carboxylate Compound>

Yield of carboxylate compound (mol %)=mol number of carboxylate compound/mol number of 2,2-dimethyl-3-methylenebicyclo[2,2,1]heptane×100

Isomer ratio (%)=mol number of 2,3,3-trimethyl-bicyclo[2,2,1]heptane-Exo-2-carboxylate/mol number of total carboxylate compounds×100

Example 1

Synthesis of Novel Carboxylate Compound

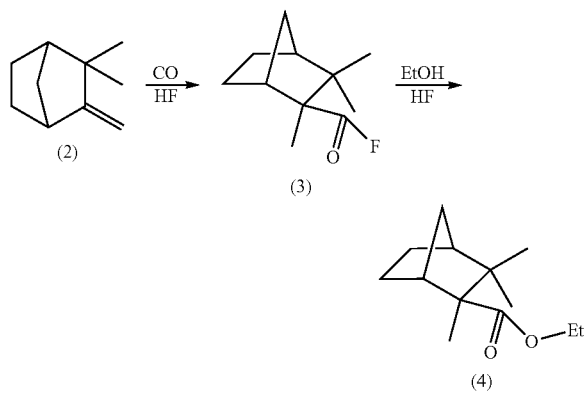

An experiment is carried out with a stainless autoclave of 500 ml capacity provided with a magnetic stirrer and three inlet upper nozzles and one lower extracting nozzle and capable of controlling an internal temperature by a jacket.

After an inside of the autoclave is first replaced with carbon monoxide, 146 g (7.3 mole) of hydrogen fluoride is introduced thereinto and a liquid temperature is made to −30° C. and then carbon monoxide is added to a pressure of 2 MPa.

A mixed solution of 66.3 g (0.49 mole) of 2,2-dimethyl-3-methylenebicyclo[2,2,1]heptane and 66.3 g of heptane is supplied to an upper part of the autoclave over 1 hour while keeping the reaction temperature at −30° C. and holding the reaction pressure at 2 MPa to conduct carbonylation reaction. After the supply of the raw material, the stirring is further continued for 15 minutes until absorption of carbon monoxide is not observed.

Then, 33.6 g (0.73 mole) of ethanol is supplied to the upper part of the autoclave while keeping the reaction temperature at 0° C. to conduct esterification for 1 hour with stirring.

The reaction liquid is extracted from the bottom of the autoclave into ice water to separate into an oil phase and an aqueous phase, and the oil phase is washed with 100 ml of an aqueous solution of 2 mass % sodium hydroxide twice and with 100 ml of a distilled water twice and dehydrated with 10 g of anhydrous sodium sulfate. The thus obtained liquid is analyzed by a gas chromatography according to an internal standard method. As a result, the yield of the carboxylate compound is 89.7 mol % (based on 2,2-dimethyl-3-methylenebicyclo[2,2,1]heptane) and the yield of the main product is 82.4 mol % (based on 2,2-dimethyl-3-methylenebicyclo[2,2,1]heptane, isomer ratio: 91.8%).

After a low-boiling fractions are removed by an evaporator, the resulting liquid is subjected to rectification with a rectifier having a theoretical plate number of 20 (distilling temperature: 157° C., vacuum degree: 60 torr), whereby a main distillate having a purity of 92.0 mass % is obtained in a yield of 75.0 g (distillation yield: 89.0 mol %).

The resulting distillate has a brisk pine-like odor.

As analyzed by GC-MS, the target product has a molecular weight of 210. Also, chemical shift values of $^1$H-NMR in a heavy chloroform solvent (δ ppm, based on TMS) are 1.11 (s, 6H), 1.27 (m, 2H), 1.30 (t, 4H), 1.34 (s, 3H), 1.42 (m, 1H), 1.52 (m, 2H), 1.55 (t, 1H), 2.06 (m, 1H) and 4.12 (m, 2H), from which the product is identified to be 2,3,3-trimethyl-bicyclo[2,2,1]heptane-Exo-2-ethylcarboxylate of the equation (4).

Example 2

The carbonylation, esterification and treatment of the reaction product liquid are carried out in the same manner as in Example 1 except that the carbonylation temperature is −25° C. and isopropanol is used as an alcohol used in the esterification. As a result of analysis of the resulting liquid by gas chromatography, the yield of the carboxylate compound is 87.3 mol % (based on 2,2-dimethyl-3-methylenebicyclo[2,2,1]heptane), and the yield of 2,3,3-trimethyl-bicyclo[2,2,1]heptane-Exo-2-isopropylcarboxylate as a main product is 78.7 mol % (based on 2,2-dimethyl-3-methylenebicyclo[2,2,1]heptane, isomer ratio: 90.1%).

Example 3

The carbonylation, esterification and treatment of the reaction product liquid are carried out in the same manner as in Example 1 except that the carbonylation temperature is −15° C. and n-butanol is used as the alcohol used in the esterification. As a result of analysis of the resulting liquid by gas chromatography, the yield of the carboxylate compound is 59.4 mol % (based on 2,2-dimethyl-3-methylenebicyclo[2,2,1]heptane), and the yield of 2,3,3-trimethyl-bicyclo[2,2,1]heptane-Exo-2-n-butylcarboxylate as a main product is 40.5 mol % (based on 2,2-dimethyl-3-methylenebicyclo[2,2,1]heptane, isomer ratio: 68.3%).

Example 4

Fruit-Type Perfume Composition

A fruit-type perfume composition characterized by having a plum-presenting deep sweetness can be obtained by adding 5 parts by mass of the carboxylate compound obtained in Example 1 to 95 parts by mass of a perfume composition having a composition shown in Table 1.

TABLE 1

| Ingredients compounded | parts by mass |
| --- | --- |
| dimethylbenzylcarbinyl butyrate | 60 |
| dimethylbenzylcarbinyl acetate | 10 |
| benzyl butyrate | 5 |

TABLE 1-continued

| Ingredients compounded | parts by mass |
| --- | --- |
| FRUITATE (made by KAO) | 5 |
| FLORAMAT (made by KAO) | 5 |
| benzyl alcohol | 3 |
| ethyl martol | 3 |
| γ-undecalactone | 1 |
| vanillin | 1 |
| VANITOROPE | 1 |
| rose type | 1 |
| Total | 95 |

INDUSTRIAL APPLICABILITY

The carboxylate compounds of the invention are novel in a point of having a brisk pine-like odor and have an excellent odor sustention, so that they are useful as a perfuming ingredient for a variety of products such as toiletry product, soap, clothing detergent and so on. Also, according to the production method of the carboxylate compound of the invention, it is possible to produce the carboxylate compounds in an industrially advantageous method.

The invention claimed is:

1. A carboxylate compound of formula (1):

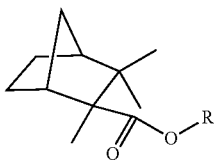

(1)

wherein R is an alkyl group having two to four carbon atoms.

2. A perfume composition, comprising the carboxylate compound of claim 1.

3. A method of producing a carboxylate compound of formula (1):

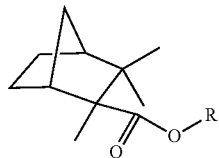

(1)

wherein R is an alkyl group having two to four carbon atoms, the method comprising:

(I) reacting 2,2-dimethyl-3-methylene bicyclo[2,2,1]heptane, which has formula (2):

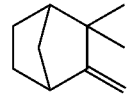

(2)

with carbon monoxide, the carbon monoxide having a partial pressure of 0.5-5 MPa; and subsequently with an alcohol having two to four carbon atoms in the presence of hydrogen fluoride.

4. The method of claim 3, wherein the partial pressure of the carbon monoxide is from 1-3 MPa.

5. The method of claim 3, where the molar amount of HF is from 4 to 25 times the molar amount of the compound of formula (2).

6. The method of claim 3, where the molar amount of HF is from 6 to 15 times the molar amount of the compound of formula (2).

7. The method of claim 3, where the alcohol is from 0.5 to 2 times the molar amount of the compound of formula (2).

8. The method of claim 3, where the alcohol is from 0.8 to 1.5 times the molar amount of the compound of formula (2).

9. The method of claim 3, wherein the reaction with the carbon monoxide is carried out at a temperature from −30 to 20° C.

10. The method of claim 3, wherein the reaction with the carbon monoxide is carried out at a temperature from −30 to −15° C.

\* \* \* \* \*